(12) United States Patent
Stigall et al.

(10) Patent No.: US 11,103,687 B2
(45) Date of Patent: *Aug. 31, 2021

(54) TREATMENT CATHETER INCLUDING THERAPEUTIC ENERGY DELIVERY

(71) Applicant: KONINKLIJKE PHILIPS N.V, Eindhoven (NL)

(72) Inventors: Jeremy Stigall, Carlsbad, CA (US); Eric Johnson, Woodside, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 104 days.

This patent is subject to a terminal disclaimer.

(21) Appl. No.: 16/392,198

(22) Filed: Apr. 23, 2019

(65) Prior Publication Data

US 2019/0247639 A1 Aug. 15, 2019

Related U.S. Application Data

(63) Continuation of application No. 15/036,914, filed as application No. PCT/US2014/066147 on Nov. 18, 2014, now Pat. No. 10,434,295.

(Continued)

(51) Int. Cl.
| | |
|---|---|
| *A61M 37/00* | (2006.01) |
| *A61M 25/00* | (2006.01) |
| *A61B 18/14* | (2006.01) |
| *A61N 7/02* | (2006.01) |
| *A61N 7/00* | (2006.01) |

(Continued)

(52) U.S. Cl.
CPC ......... *A61M 37/0092* (2013.01); *A61B 18/04* (2013.01); *A61B 18/1492* (2013.01); *A61M 25/0043* (2013.01); *A61N 7/00* (2013.01); *A61N 7/02* (2013.01); *A61B 18/08* (2013.01); *A61B 18/245* (2013.01); *A61B 2018/0041* (2013.01); *A61M 25/007* (2013.01); *A61M 2025/0057* (2013.01); *A61M 2025/0081* (2013.01);

(Continued)

(58) Field of Classification Search
CPC .......... A61M 37/0092; A61M 25/0043; A61B 18/04; A61B 18/1492; A61N 7/00; A61N 7/02
USPC .......................................................... 604/21
See application file for complete search history.

(56) References Cited

U.S. PATENT DOCUMENTS

| | | | |
|---|---|---|---|
| 4,867,141 A | | 9/1989 | Nakada |
| 4,998,933 A | * | 3/1991 | Eggers ............... A61B 18/1492 604/114 |

(Continued)

FOREIGN PATENT DOCUMENTS

WO    1991/012770    9/1991

OTHER PUBLICATIONS

Tapson, Victor F. "Thrombolytic Therapy for Acute Pulmonary Embolishm" Seminars in Thrombosis and Hemostasis, vol. 39, No. 4. 2013.

*Primary Examiner* — Phillip A Gray

(57) ABSTRACT

The invention includes catheters that have therapeutic agent- and therapeutic energy-delivery capability. In particular embodiments, the catheters include only a single therapeutic energy transducer that is configured to deliver energy to over half of the circumference of the catheter. The therapeutic catheters of the invention allow for faster and more effective thrombus removal because of the simultaneous delivery of therapeutic agents and energy.

18 Claims, 4 Drawing Sheets

Related U.S. Application Data

(60) Provisional application No. 61/905,351, filed on Nov. 18, 2013.

(51) Int. Cl.
*A61B 18/04* (2006.01)
*A61B 18/08* (2006.01)
*A61B 18/24* (2006.01)
*A61B 18/00* (2006.01)

(52) U.S. Cl.
CPC .. *A61M 2205/05* (2013.01); *A61N 2007/0043* (2013.01); *A61N 2007/0078* (2013.01)

(56) References Cited

U.S. PATENT DOCUMENTS

| | | | |
|---|---|---|---|
| 6,024,718 A * | 2/2000 | Chen | A61B 17/2202 604/22 |
| 8,449,467 B2 | 5/2013 | Wilser | |
| 2001/0041880 A1 * | 11/2001 | Brisken | A61N 7/022 604/503 |
| 2004/0143256 A1 | 7/2004 | Bednarek | |
| 2008/0221506 A1 * | 9/2008 | Rodriguez | A61N 7/00 604/22 |
| 2009/0112150 A1 * | 4/2009 | Unger | A61M 37/0092 604/22 |
| 2009/0254078 A1 | 10/2009 | Just | |
| 2010/0286684 A1 | 11/2010 | Hata | |
| 2011/0060212 A1 | 3/2011 | Slee | |
| 2013/0150715 A1 * | 6/2013 | Lacoste | A61B 8/4483 600/439 |

* cited by examiner

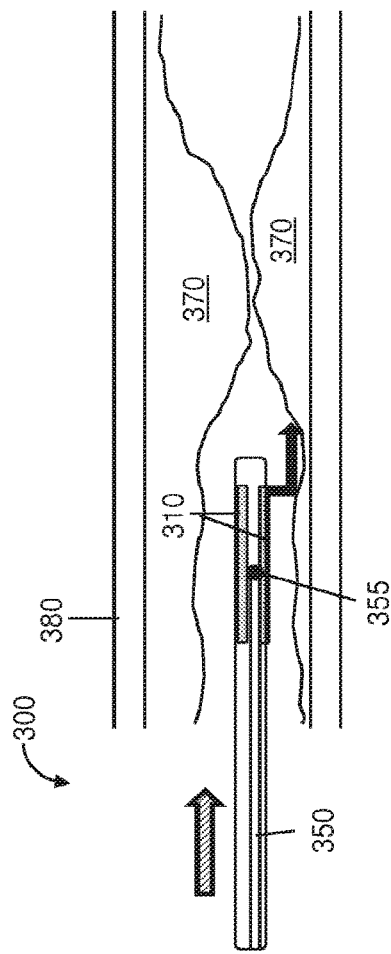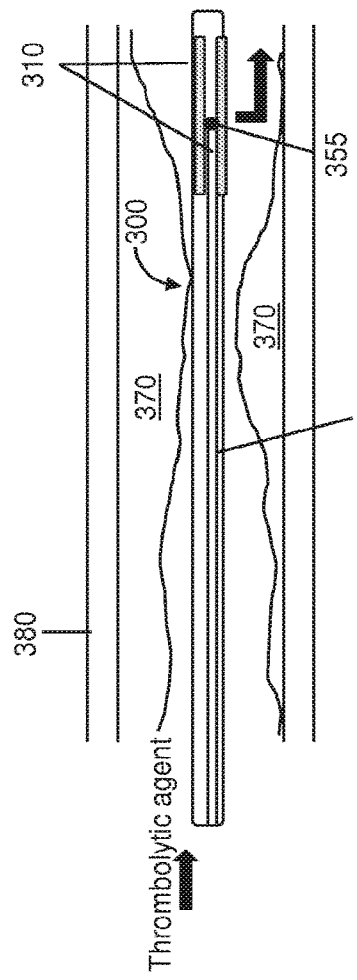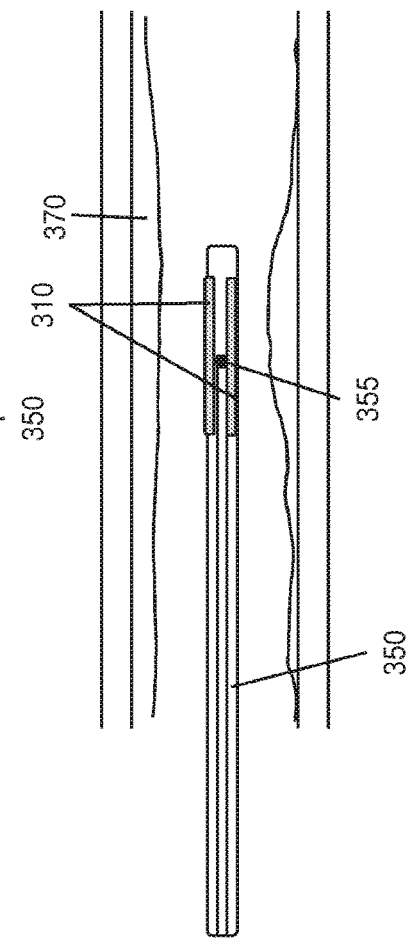

TREATMENT CATHETER INCLUDING THERAPEUTIC ENERGY DELIVERY

RELATED APPLICATIONS

This application is a continuation of U.S. patent application Ser. No. 15/036,914, filed May 16, 2016, which is a national stage application of PCT Application Serial No. PCT/US14/66147, filed Nov. 18, 2014, which claims priority to U.S. Patent Application Ser. No. 61/905,351, filed Nov. 18, 2013, all of which are incorporated herein by reference in their entirety.

FIELD OF THE INVENTION

The invention relates to medical devices, such as vascular catheters, that are capable of simultaneously delivering therapeutic agents and therapeutic energy to a targeted tissue, such as thrombus.

BACKGROUND

Thrombosis is a medical condition that results from the formation of a blood clot, or thrombus, within a vessel. Thrombi often develop in the valves, legs, or other lower abdomen (i.e. deep vein thrombosis), but may occur in other vessels. The clot is typically formed from a pooling of blood within the vein due to abnormally long periods of rest, e.g. when an individual is bed ridden following surgery or suffering a debilitating illness. In addition to thrombosis, atherosclerosis is another medical condition that results from the formation of a blockage in a vein. The atherosclerosis is due to the build of atheroma material along the arterial walls. Atheroma deposits can have widely varying properties, with some deposits being relatively soft and others being fibrous and/or calcified. In the latter case, the deposits are frequently referred to as plaque. Often thrombosis and atherosclerosis are both present in the veins. For example, a thrombus develops around the atherosclerotic plaque.

The formation of thrombi and build-up of plaque can lead to a stroke or embolism that may lead to serious health issues, including death. Strokes occur when the blood clot or plaque blocks an artery supplying blood to the brain, thus depriving the brain tissue of oxygen. Without oxygen, brain cells begin to die. Embolisms occur when a blood clot travels around the body and lodges itself in an organ. For example, a pulmonary embolism is a blockage of the blood supply to the lungs that causes severe hypoxia and cardiac failure.

A variety of interventional catheterization techniques are available to directly address thrombi and plaque build-up. These techniques may be combined with other treatments, such as administration of anticoagulants or statins. Many of the interventional techniques are complicated and require advanced medical facilities and substantial training for proper use. Additionally, some interventional catheters currently on the market are overly-complicated and fragile, making interventional procedures time-consuming and costly.

SUMMARY

The invention is a treatment catheter capable of delivering therapeutic agents, such as thrombolytic agents, and therapeutic energy, such as acoustic or thermal energy, simultaneously. The catheters of the invention, thus, reduce the number of catheter exchanges that are needed to treat vasculature as opposed to known methods that use two separate catheters for therapeutic energy and therapeutic agent delivery. In some embodiments, the catheter includes only a single therapeutic energy transducer, greatly simplifying the design of the catheter, resulting in a more robust device that is simple to use and effective at treating targeted tissues. This design also allows the catheters to be produced more economically, making the procedure available for more patients. In some embodiments, the single therapeutic energy transducer is configured to deliver therapeutic energy over an angular distribution that is greater than one half of the circumference of the catheter. Devices of the invention may be used for other medical procedures that benefit from the combination of therapeutic agent delivery and therapeutic energy delivery, such as treatment of tumors that are accessible from the vasculature.

In an embodiment, the invention is a catheter having a flexible elongated body having a plurality of openings at a distal end of the body, and a lumen in fluid communication with at least one of the openings and with a port at the proximal end of the body. The body additionally includes a singular therapeutic energy transducer at the distal end of the body, wherein the transducer is configured to deliver therapeutic energy to a target tissue within the vasculature while a therapeutic agent is delivered to the target via the openings. The openings may be interspersed with the therapeutic energy transducer(s), or the openings may be located distal or proximal to the therapeutic energy transducer(s). In some embodiments, the single therapeutic energy transducer is configured to deliver therapeutic energy over an angular distribution that is greater than one half of the circumference of the catheter.

The invention additionally includes methods of treatment using the disclosed catheters. Such methods include inserting a catheter disclosed herein into a lumen of a vessel (i.e., vasculature) identified as needing assessment and treatment. Once in the presence of the targeted tissue, therapeutic agents, e.g., thrombolytic agents, are delivered simultaneously with therapeutic energy, e.g., acoustic energy. After treatment, the vessel may be imaged or otherwise assessed for the success of the treatment.

The invention also includes systems for treating vasculature. In an embodiment, a system includes a catheter having a flexible elongated body having a plurality of openings at a distal end of the body and a lumen in fluid communication with at least one of the openings and with a port at the proximal end of the body. The catheter additionally includes a single therapeutic energy transducer at the distal end of the body that is configured to deliver therapeutic energy to a target within the vasculature while a therapeutic agent is delivered to the target via the openings. The system additionally includes a therapeutic energy controller operatively coupled to the therapeutic energy transducer and configured to control the energy delivered to the target, and a fluid delivery subsystem operatively coupled to the port and configured to control the delivery of therapeutic agents to the target. In an embodiment, the therapeutic energy transducer is an acoustic energy transducer. In an embodiment, the fluid delivery subsystem includes a syringe or a pump.

BRIEF DESCRIPTION OF THE DRAWINGS

FIG. 3A illustrates the use of a catheter of the invention to reduce thrombus in a vessel;

FIG. 3B illustrates the use of a catheter of the invention to reduce thrombus in a vessel;

FIG. 3C illustrates the use of a catheter of the invention to reduce thrombus in a vessel;

DETAILED DESCRIPTION

Figure 1:
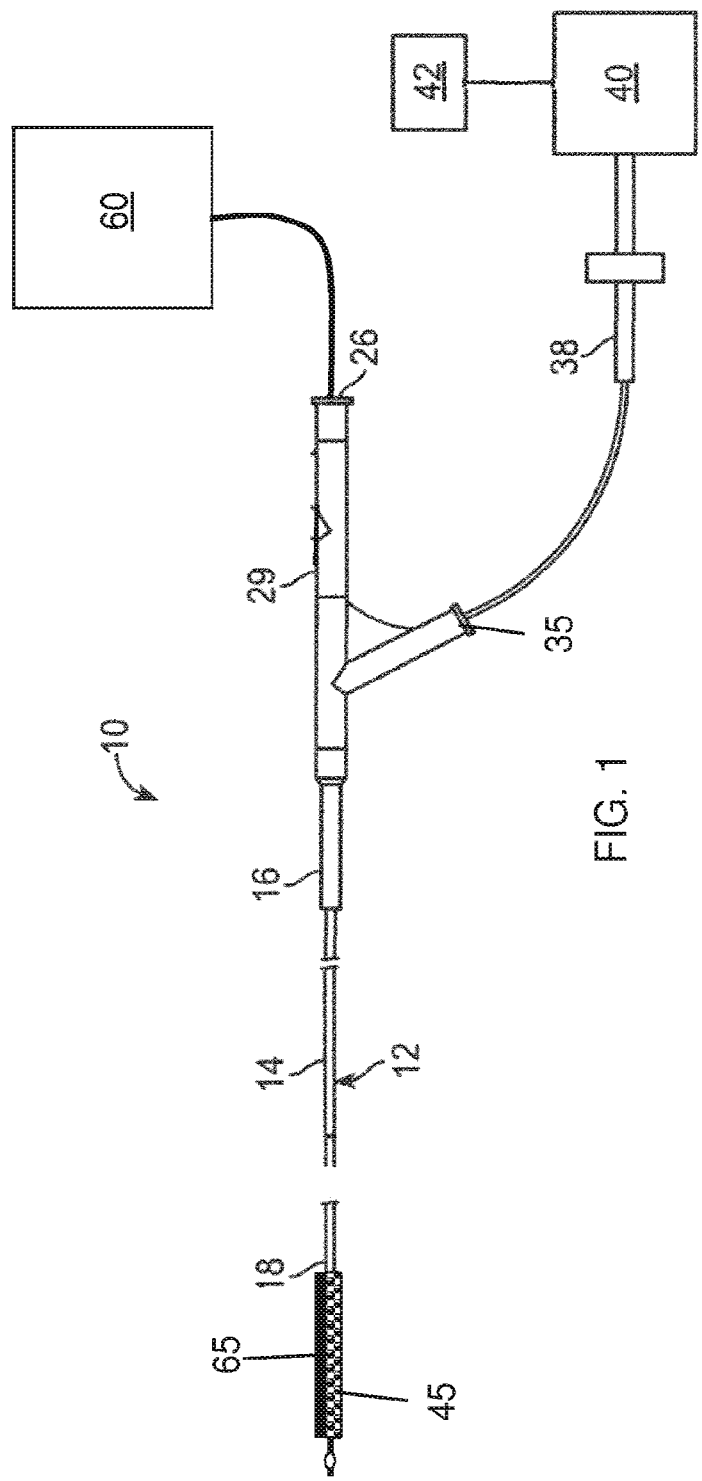
FIG. 1 depicts a catheter of the invention and associated subsystems for controlling the functionality of the catheter.

The invention includes medical devices, such as catheters, that have therapeutic agent and therapeutic energy delivery capability. In particular embodiments, the catheters include only a single therapeutic energy transducer that is configured to deliver energy to over half of the circumference of the catheter. The therapeutic catheters of the invention allow for faster and more effective thrombus removal because of the simultaneous delivery of therapeutic agents and energy.

Catheters of the invention find uses for multiple medical procedures, such as removal of thrombus or plaque from veins and arteries. The catheters may be delivered through a number of entry points, such as the femoral or radial arteries. The catheters may be guided to the area for treatment with one or more external imaging systems, such as fluoroscopy, CAT, or MRI. Typically, the catheter will be guided along a guide wire to the tissues targeted for treatment. The catheters may be used in conjunction with other procedures or catheters such as imaging catheters or aspiration catheters. The catheters of the invention are not limited to treating diseased vasculature, however. The catheters can be used, for example, for treating tumors that are accessible through the vasculature.

In some embodiments, the catheters of the invention are used to deliver thrombolytic agents, i.e., chemicals or compositions designed to erode, disrupt, or dissolve clotted blood, plaque, and/or fatty materials. Thrombolytic agents suitable for use with catheters of the invention include streptokinases, urokinases, and tissue plasminogen activators (TPAs) such as alterplase, reteplase, and teneteplase. The thrombolytic agents may be isolated from organisms where the agents naturally occur, such as *Streptococcus*, or they may be generated recombinantly and purified. In some embodiments, thrombolytic agents may be administered in conjunction with anticoagulants, such as heparin or Warfarin™. (Coumadin), or factor Xa inhibitors, such as rivaroxaban or apixaban.

Catheters of the invention include therapeutic energy transducers for delivering therapeutic energy to tissue in need of treatment, for example, veins having clotted blood or accumulated fatty material. The therapeutic energy may be acoustic energy, thermal energy, or electromagnetic radiation. Accordingly, suitable transducers will be incorporated into catheters of the invention to achieve the desired therapeutic energy. For example, acoustic energy can be delivered from the distal end of a catheter by incorporating ultrasonic transducers that operate between about 20 kHz and about 50 MHz. Such transducers are commercially-available from suppliers such as APC International (Mackeyville, Pa.). In some instances, a single larger transducer can be used to deliver energy over a suitable length of the catheter, for example, at least about 1 cm in length, i.e., at least about 2 cm in length, i.e., at least about 3 cm in length, i.e., at least about 5 cm in length. Thermal transducers suitable for incorporation into catheters of the invention typically use resistive heating to heat an element, whereupon the heat from the element is radiated to the surrounding tissue. Electromagnetic radiation, such as infrared radiation, may be delivered with microlasers or light-emitting diodes (LEDs).

In certain embodiments, the devices and methods of the present invention are designed to dissolve blood clots, such as such as emboli and thrombi and other occlusive material from body lumens. The defect in the body lumen can be a de novo clot or caused by prior intervention, e.g., a clot caused by a stent. The devices and methods, however, are also suitable for treating stenosis of body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Delivery of therapeutic agents to such material can thus be beneficial to maintain patency of the body lumen. While the remaining discussion is directed at therapeutic treatment of athermanous or thrombotic occlusive material in an artery, it will be appreciated that the systems, devices, and methods of the present invention can be used to treat and/or pass through a variety of occlusive, stenotic, or hyperplastic material in a variety of body lumens.

A catheter 10 of the invention, configured to treat tissues, is shown in FIG. 1. The catheter 10 includes a body having proximal 16, middle 14, and distal 18 portions. The catheter 10 includes a therapeutic energy transducer 65 located at the distal-most end of the catheter body. A plurality of openings 45, through which therapeutic agents can be delivered to targeted vasculature, is located opposite of the therapeutic energy transducer 65. As shown in FIGS. 2A-2D, the orientations of the therapeutic energy transducer 65 and the openings 45 are not limited to the configuration shown in FIG. 1. Additionally, the therapeutic energy transducer 65 and the openings 45 need not occupy the same length of the catheter. That is, the openings 45 may be distal-most, or the therapeutic energy transducer 65 can be distal-most.

As shown in FIG. 1, the therapeutic energy transducer 65 and the openings 45 are connected to subsystems that are located outside of the body and interfaced via interface 29. For example, as shown in FIG. 1, the therapeutic energy transducer 65 is connected to the therapeutic energy controller 60, which controls the power and duration of the energy that is delivered to the targeted tissue. Additionally, as shown in FIG. 1, the openings 45 at the distal end of the body are connected via an interior lumen 12 within the catheter body to a port 35 at the proximal end. As shown in FIG. 1, the port 35 is connected via tubing to a fluid delivery subsystem that may include a pump 40 connected to a reservoir 42 that contains a therapeutic agent to be delivered to the targeted vasculature. In some embodiments the therapeutic energy controller 60 and the pump 40 may be interfaced to a higher level controller (not shown) that coordinates delivery of therapeutic energy and agents. In some embodiments, the therapeutic energy and agents may be delivered simultaneously. In some embodiments, the therapeutic energy and agents may be delivered at different times. In some embodiments, the therapeutic agents are delivered continuously and the therapeutic energy is pulsed. In some embodiments, the therapeutic agents and the therapeutic energy are delivered at a rate that decreases with time.

While not shown, it is understood that catheters of the invention typically include a guide wire lumen that allows the catheter to be directed to a point of treatment. The guide wire lumen may be a distinct guide wire lumen that runs the length of the catheter. In other embodiments, the guide wire lumen may only run a portion of the length of the catheter, e.g., a "rapid exchange" guide wire lumen. The guide wire lumen may be situated on top of the therapeutic delivery lumen or the guide wire channel could be side-by-side the therapeutic delivery lumen. In other cases, it may be possible to provide a fixed or integral coil tip or guide wire tip on the distal portion of the catheter or even dispense with the guide wire entirely. For convenience of illustration, guide wires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French.

Catheter bodies will typically be composed of a biocompatible polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

The distal portion of the catheters of the present invention may have a wide variety of forms and structures. In many embodiments, a distal portion of the catheter is more rigid than a proximal portion, but in other embodiments the distal portion may be equally as flexible as the proximal portion. One aspect of the present invention provides catheters having a distal portion with a reduced rigid length. The reduced rigid length can allow the catheters to access and treat tortuous vessels and small diameter body lumens. In most embodiments a rigid distal portion or housing of the catheter body will have a diameter that generally matches the proximal portion of the catheter body, however, in other embodiments, the distal portion may be larger or smaller than the flexible portion of the catheter.

In some embodiments, the catheter may include a flexible atraumatic distal tip coupled to the rigid distal portion of the catheter. For example, an integrated distal tip can increase the safety of the catheter by eliminating the joint between the distal tip and the catheter body. The integral tip can provide a smoother inner diameter for ease of tissue movement into a collection chamber in the tip. During manufacturing, the transition from the housing to the flexible distal tip can be finished with a polymer laminate over the material housing. No weld, crimp, or screw joint is usually required. The atraumatic distal tip permits advancing the catheter distally through the blood vessel or other body lumen while reducing any damage caused to the body lumen by the catheter. Typically, the distal tip will have a guide wire lumen to permit the catheter to be guided to the target tissue over a guide wire. In some exemplary configurations, the atraumatic distal tip includes a coil. In some configurations the distal tip has a rounded, blunt distal end.

A variety of configurations may be used for catheters of the invention, as shown in FIGS. 2A-2D. Each of FIGS. 2A-2D shows an exemplary distal end 210-240 of a catheter of the invention, including a therapeutic energy transducer 250 and one or more openings 270 for delivering therapeutic agents. As shown in FIGS. 2A-2D, each of the openings 270 is connected to a lumen 280 which runs through the catheter body and connects to a port at the proximal end (not shown) thereby allowing therapeutic agents to be delivered via the openings 270 to targeted tissues. In some embodiments, the catheter will include a single therapeutic energy transducer 250, such as shown in FIGS. 2A-2D. It is to be recognized, that catheters of the invention may include multiple therapeutic energy transducers 250, using configurations similar to FIGS. 2A-2D.

In particular, therapeutic catheter end 210 may include a single helically-wound therapeutic energy transducer 250, with openings 270 distributed along the tip between the coils of the helix. In other embodiments, such as shown in FIG. 2B, therapeutic catheter end 220 includes a single therapeutic energy transducer 250 that covers more than half of the circumference of the catheter with an open portion where the openings 270 are configured to deliver therapeutic agents. In FIG. 2C, therapeutic catheter end 230 includes a single therapeutic energy transducer 250 that leaves a diamond pattern of open portions, where openings 270 are located and configured to deliver therapeutic agents. In FIG. 2D, therapeutic catheter end 240 includes a single therapeutic energy transducer 250 that covers most of the circumference of the catheter with open portions where the openings 270 are configured to deliver therapeutic agents.

Figure 2A:
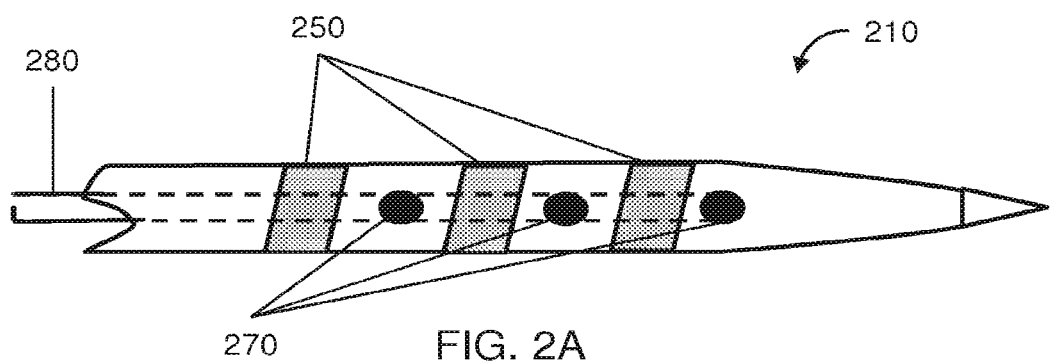
FIG. 2A depicts an arrangement of a therapeutic energy transducer and openings for delivering a therapeutic agent.
Figure 2B:
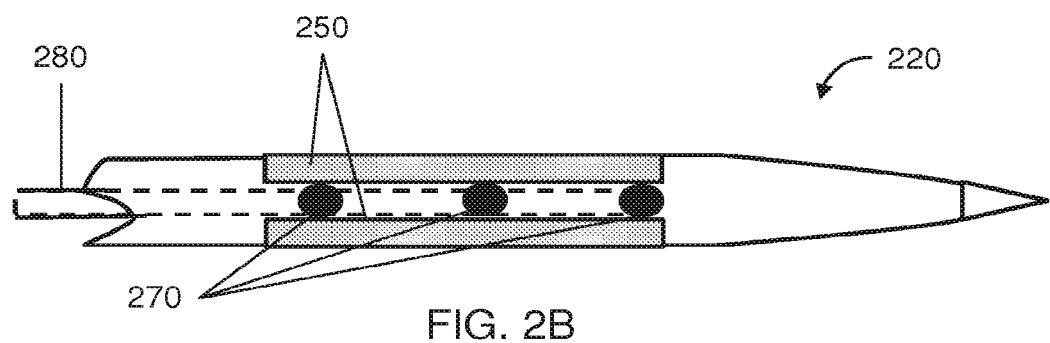
FIG. 2B depicts an arrangement of a therapeutic energy transducer and openings for delivering a therapeutic agent.
Figure 2C:
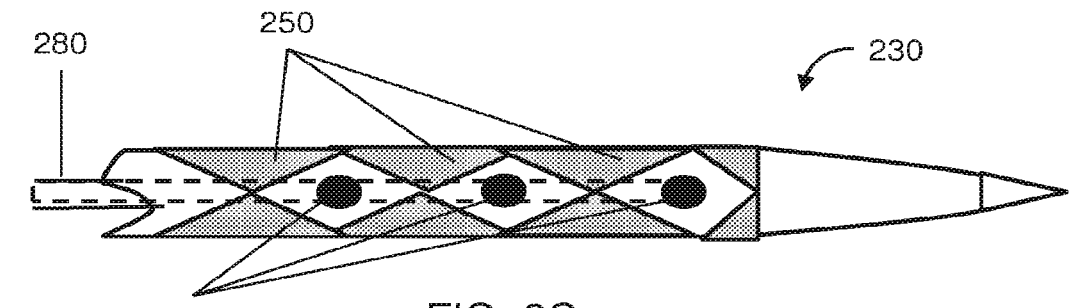
FIG. 2C depicts an arrangement of a therapeutic energy transducer and openings for delivering a therapeutic agent.
Figure 2D:
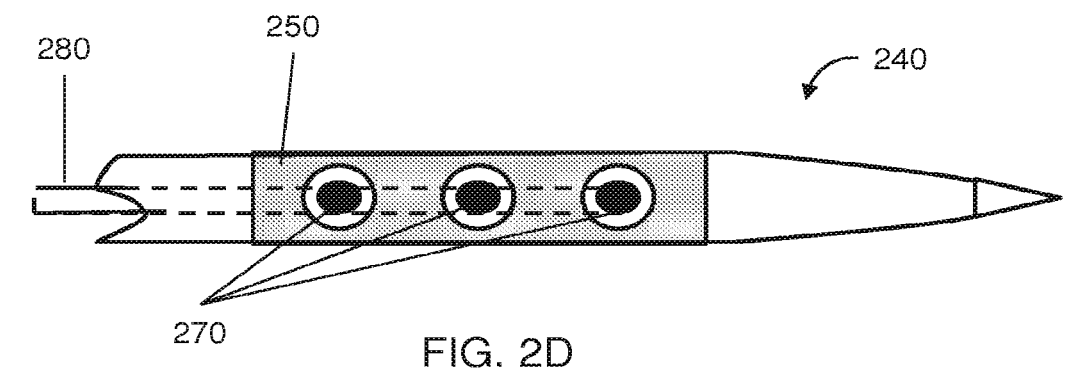
FIG. 2D depicts an arrangement of a therapeutic energy transducer and openings for delivering a therapeutic agent.

The catheter ends 210-240 shown in FIG. 2A require fewer electrical connections than other therapeutic energy/therapeutic agent delivery catheters that include multiple distributed therapeutic energy transducers. Accordingly, there are fewer connections to be made between the distal and proximal ends of the catheter, reducing the complexity of the device and resulting in a more robust and economic catheter. Additionally, the reduced number of connections facilitate construction of smaller catheters that can be used access to smaller peripheral veins and arteries. The reduced connections also reduce the complexity of the electrical connectors at the proximal end of the device. By using a single therapeutic energy transducer with a configuration shown in FIGS. 2A-2D, therapeutic energy can be delivered to an angular distribution of over half of the circumference of the catheter. For example, the configurations in FIGS. 2A, 2C, and 2D, allow therapeutic energy to be delivered around the entire circumference of the catheter.

A method of using a catheter of the invention is depicted in FIGS. 3A-3C. In FIGS. 3A-3C, a catheter 300 capable of delivering therapeutic energy and therapeutic agents is shown in three separate steps of the treatment. Similar to FIGS. 1 and 2A-2D, catheter 300 includes a body that has a therapeutic energy transducer 310 and an opening 355 at the distal end of the catheter. (It is to be appreciated that catheters having multiple openings 355, e.g., configured as shown in FIGS. 2A-2D, are also suitable for use with the methods depicted in FIGS. 3A-3C.) An interior lumen 350 is coupled to the opening 355, and allows a therapeutic agent to be delivered to the thrombus 370 from a port (not shown) at the proximal end of the catheter 300. As shown in FIG.

3A, the catheter 300 is moved to the location of a blockage. The blockage may have been identified prior to the procedure using, e.g., a radiopaque dye and fluoroscopy. Once in the presence of the blockage, a thrombolytic agent can be delivered with the catheter 300 along with therapeutic energy. The thrombolytic agent and energy causes the dissolution of a portion of the thrombus 370, allowing the catheter 300 to pass through the narrowed area, as shown in FIG. 3B. Once the catheter 300 can pass through the narrowing, the thrombolytic agent and energy can be delivered to the other side of the blockage, resulting in additional thrombus 370 removal. By moving the catheter 300 through the narrowing while delivering thrombolytic agent and energy, the narrowed section is eventually opened to nearly normal, as shown in FIG. 3C. In some embodiments, the catheter 300 will be removed and a secondary imaging catheter (not shown) can be used to evaluate the effectiveness of the procedure.

Figure 4:
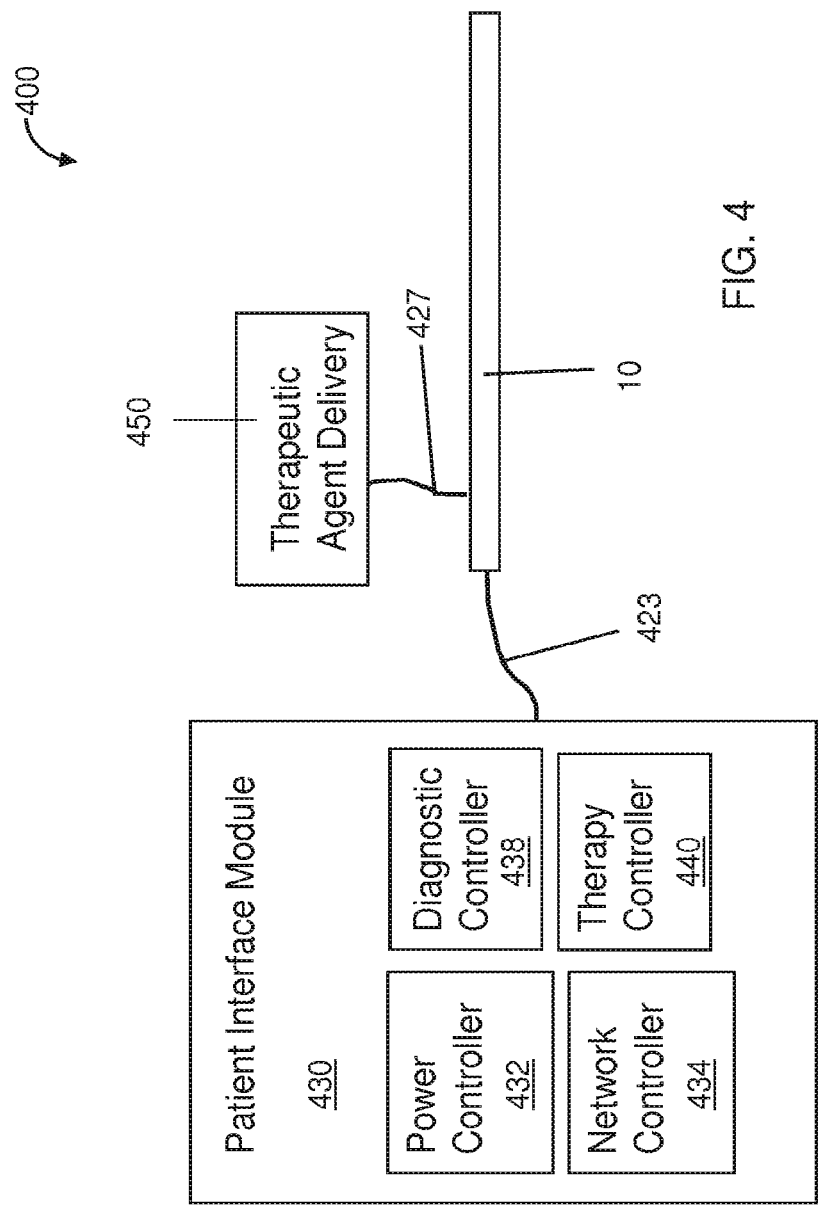
FIG. 4 depicts a system of the invention configured to treat vasculature.

The disclosed catheters make up a part of a system 400 for treating vasculature, e.g., thrombus, e.g., deep-vein thrombosis. The system 400 includes a catheter 10 having openings and a therapeutic energy transducer of the type described previously. The therapeutic energy transducer and the openings may be arranged in a variety of configurations, e.g., as depicted in FIGS. 2A-2D. As shown in FIG. 4, the system additionally includes a subcontroller for each function, i.e., a therapeutic agent delivery controller 150 and a therapeutic energy controller 440. A system 400 of the invention may also include diagnostic sensors, such as pressure, flow, or temperature sensors (not shown) that are interfaced to a diagnostic controller 438. In some embodiments, the various subcontrollers are operatively connected to a global system controller (not shown) that coordinates all of the functionality. The global system controller may also synchronize the functionality of the various functionality of the system, as discussed previously. In order to facilitate use of a system of the invention, various subcontrollers may be tied to a Patient Interface Module 430 that allows connectivity of all of the various subcontrollers to other devices with only one or two connections. In some embodiments, the Patient Interface Module 430 may include a network controller 434 that allows the Patient Interface Module 430 to be controlled via a networked connection.

Accordingly, the invention includes catheters that can be used to simultaneously delver energy and therapeutic energy to vasculature. Other uses of devices of the invention will be evident to those of skill in the art in view of the disclosure, claims, and figures herein.

EQUIVALENTS

Various modifications of the invention and many further embodiments thereof, in addition to those shown and described herein, will become apparent to those skilled in the art from the full contents of this document. The subject matter herein contains important information, exemplification and guidance that can be adapted to the practice of this invention in its various embodiments and equivalents thereof.

What is claimed is:

1. A catheter for administering therapy to vasculature, comprising:
   a flexible elongated body having a plurality of openings at a distal end of the flexible elongated body;
   a lumen in fluid communication with at least one of the openings, wherein the at least one of the openings has a size and shape; and
   a therapeutic energy transducer disposed at the distal end of the flexible elongated body, the therapeutic energy transducer comprising at least one open portion, wherein at least a portion of the at least one of the openings aligns with at least a portion of the at least one open portion of the therapeutic energy transducer thereby allowing delivery of a therapeutic agent during delivery of energy to a target within the vasculature, wherein the at least one open portion has a size and shape, wherein the size or shape of the at least one open portion is different than the size or shape of the at least one of the openings.

2. The catheter of claim 1, wherein the therapeutic energy transducer is a singular therapeutic energy transducer.

3. The catheter of claim 2, wherein the distal portion of the flexible elongated body has a circumference, and the singular therapeutic energy transducer is configured to deliver energy over greater than half of the circumference.

4. The catheter of claim 1, wherein the distal portion of the flexible elongated body has a circumference, and the therapeutic energy transducer is configured to deliver energy over greater than half of the circumference.

5. The catheter of claim 1, wherein the therapeutic energy transducer is aligned parallel to the longitudinal axis of the flexible elongated body.

6. The catheter of claim 1, wherein the therapeutic energy transducer comprises a helical shape, wherein the helical shape comprises an axis collinear with the longitudinal axis of the flexible elongated body.

7. The catheter of claim 1, wherein the therapeutic energy transducer is configured to deliver ultrasonic energy to the target.

8. The catheter of claim 1, wherein the at least one open portion of the therapeutic energy transducer comprises a diamond shape.

9. The catheter of claim 1, wherein the at least one open portion of the therapeutic energy transducer comprises a circular shape.

10. The catheter of claim 9, wherein the at least one of the openings comprises a circular shape.

11. The catheter of claim 1, wherein the at least one of the openings comprises a circular shape.

12. The catheter of claim 11, wherein the at least one open portion of the therapeutic energy transducer comprises a rectangular shape.

13. The catheter of claim 1, wherein the size of the at least one open portion of the therapeutic energy transducer is greater than the size of the at least one of the openings.

14. A system for administering therapy to vasculature, comprising:
   a catheter comprising a flexible elongated body having a plurality of openings at a distal end of the flexible elongated body, a lumen in fluid communication with at least one of the openings, wherein the at least one of the openings has a size and shape, and a therapeutic energy transducer disposed at the distal end of the flexible elongated body, the therapeutic energy transducer comprising at least one open portion, wherein at least a portion of the at least one of the openings aligns with at least a portion of the at least one open portion of the therapeutic energy transducer thereby allowing delivery of a therapeutic agent during delivery of energy to a target within the vasculature, wherein the at least one open portion has a size and shape, wherein the size or shape of the at least one open portion is different than the size or shape of the at least one of the openings;

a therapeutic energy controller operatively coupled to the therapeutic energy transducer and configured to control the energy delivered to the target; and a fluid delivery subsystem fluidly coupled to the catheter and configured to control the delivery of the therapeutic agent to the catheter.

15. The system of claim 14 further comprising diagnostic sensors.

16. The system of claim 14, wherein the therapeutic energy transducer is a singular therapeutic energy transducer.

17. The system of claim 14, wherein the distal portion of the flexible elongated body has a circumference, and the singular therapeutic energy transducer is configured to deliver energy over greater than half of the circumference.

18. The system of claim 14, wherein the distal portion of the flexible elongated body has a circumference, and the therapeutic energy transducer is configured to deliver energy over greater than half of the circumference.

* * * * *